United States Patent [19]

Arison et al.

[11] Patent Number: 4,975,372
[45] Date of Patent: Dec. 4, 1990

[54] MICROBIAL TRANSFORMATION PRODUCT OF L-683,590

[75] Inventors: Byron H. Arison, Watchung; Edward S. Inamine, Rahway; Shieh-Shung T. Chen, Morganville; Linda S. Wicker, Westfield, all of N.J.

[73] Assignee: Merck & Co., Inc., Rahway, N.J.

[21] Appl. No.: 297,631

[22] Filed: Jan. 13, 1989

[51] Int. Cl.$^5$ .................... C12P 17/18; C07D 498/18; A61K 31/395
[52] U.S. Cl. .................... 435/119; 435/128; 435/826; 540/456; 540/457; 514/183
[58] Field of Search ............... 540/457, 456; 514/183; 435/119, 128, 826

[56] References Cited

U.S. PATENT DOCUMENTS 4,894,366  1/1990  Okuhara et al. .................... 540/456

Primary Examiner—Robert T. Bond
Attorney, Agent, or Firm—Robert J. North; Hesna J. Pfeiffer

[57] ABSTRACT

Described is a new immunosuppressant, L-685,487, a monodemethylated rearranged derivative of L-683,590, produced under fermentation conditions utilizing the microorganism, unidentified Actinomycete (Merck Cultrue Collection MA 6474) ATCC No. 53828. The macrolide immunosuppressant is useful in preventing human host rejection of foreign organ transplants, e.g. bone marrow and heart transplants.

7 Claims, 2 Drawing Sheets

MICROBIAL TRANSFORMATION PRODUCT OF L-683,590

BACKGROUND OF THE INVENTION

1. Field of the Invention

This invention relates to a new immunosuppressant agent, L-685,487, and a fermentation process for its production utilizing the microorganism unidentified Actinomycete (MA 6474), ATCC No. 53828. The process involves culturing the microorganism and L-683,590 under conditions which rearranges and monodemethylates the structure of L-683,590. Also disclosed is a method for its use in a human host for treatment of autoimmune diseases, infectious diseases and/or prevention of organ transplant rejections.

2. Brief Description of Disclosures in the Art

In 1983, the US FDA licensed cyclosporin, and extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, hereby incorporated by reference, describes a new macrolide immunosuppressant FK-506 which is reputed to be 100 times more effective than cyclosporin. The macrolide is produced by fermentation of a particular strain of *Streotomyces tsukubaensis*. Also described is the closely related macrolide immunosuppressant FK-520, produced by *S. hygroscopicus* subsp. *yakushimaensis*.

U.S. Pat. No. 3,244,592 to T. Arai describes the culturing of *Streotomyces hygroscopicus var. ascomyceticus* to produce the antifungal "ascomycin".

There is, however, no description in the literature of the production of any immunosuppressive agents, which substantially lack the side effects of cyclosporin.

Newer, safer drugs exhibiting less side effects are constantly being searched for in the field.

SUMMARY OF THE INVENTION

It has been found that a new immunosuppressant, L-685,487, can be obtained by the fermentation of the microorganism *Actinoplanacete sp.* (MA 6474), ATCC No. 53828, in the presence of the macrolide immunosuppressant L-683,590, under submerged aerobic conditions in an aqueous carbohydrate medium, containing a nitrogen nutrient, said conditions being conducted at a pH of about 7 for a sufficient time to selectively monodemethylate L-683,590 (i.e. remove the C-13 methoxyl group) and cause a rearrangement of the six-membered pyranyl ring to a five-membered furanyl ring and wherein a hydroxyl is at C-14.

The resultant L-685,487 exhibits immunosuppressive activity, i.e., positive inhibition of T-cell activation, as demonstrated by the calcium ionophore (ionomycin) plus phorbol myristate acetate (PMA) induced T-cell stimulation assay, also referred to herein as the "T-cell proliferation assay". The principle of this assay is to measure the proliferation of mouse T lymphocytes stimulated with the combination of ionomycin plus PMA. A positive sample in this assay will inhibit T-cell proliferation, as indicated by reduced tritiated thymidine uptake.

In accordance with this invention, there is provided an immunosuppressant, identified as L-685,487, produced by culturing a strain of unidentified Actinomycete (ATCC No. 53828), together with L-683,590 under submerged aerobic fermentation conditions in an aqueous carbohydrate medium, containing a nitrogen nutrient, for a sufficient time to produce product L-685,487.

Figure 1:
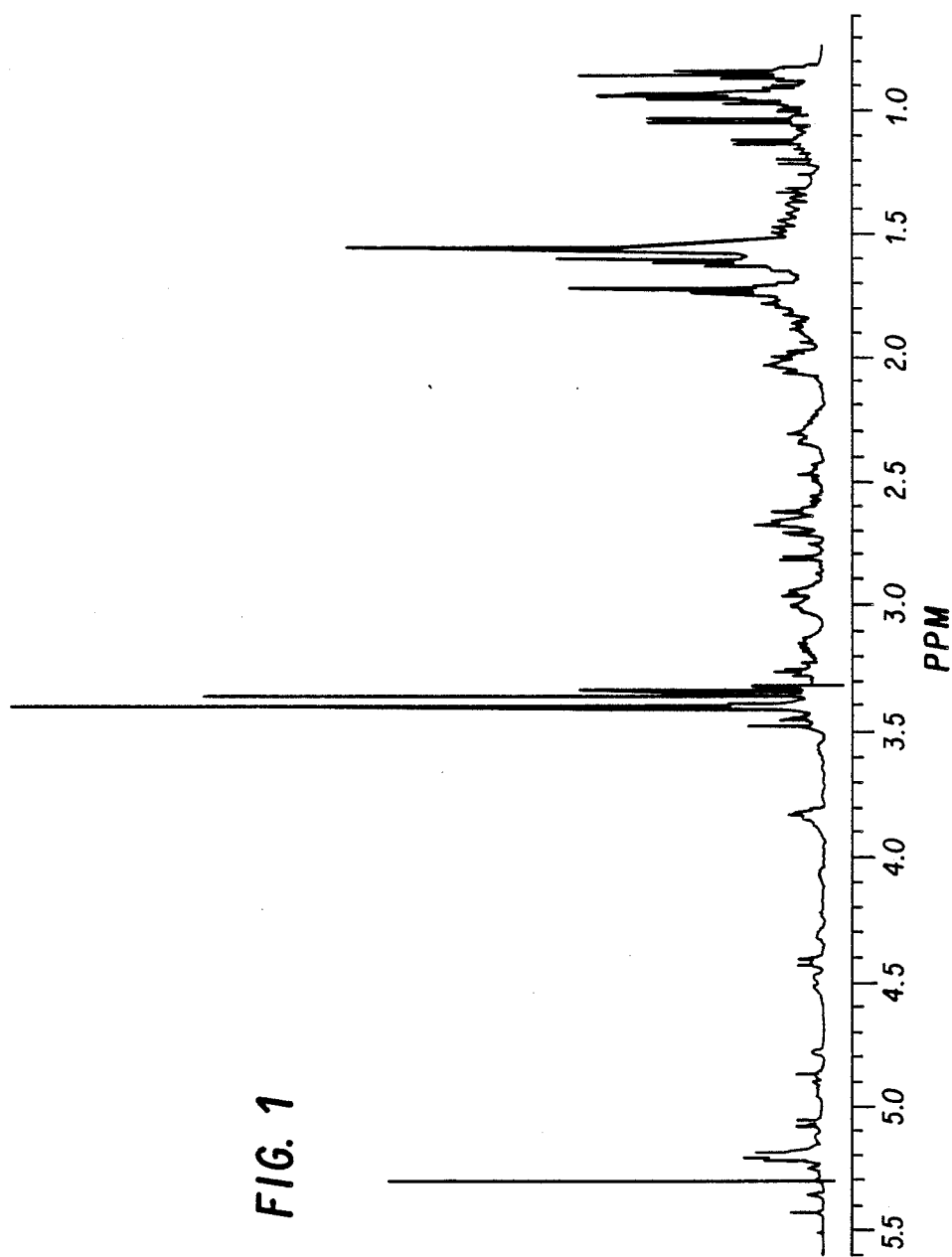
FIG. 1 is an $^1$H nuclear magnetic resonance (NMR) spectrum taken at 400 MHz of L-685,487 in CDCl$_3$.

The new immunosuppressant, L-685,487, exhibits positive inhibition of T-cell activation by the T-cell proliferation assay, exhibits a proton nuclear magnetic resonance spectrum as identified in FIG. 1, and a molecular weight of 777 as obtained by FAB mass spectrometry.

Further provided is a process for producing an immunosuppressant, identified as L-685,487, comprising the step of culturing a strain of Actinomycete ATCC No. 53828 in the presence of L-683,590 under submerged aerobic fermentation conditions in an aqueous carbohydrate medium containing a nitrogen nutrient at a pH below 8.0 for a sufficient time to produce L-685,487.

Furthermore, there is provided a broth produced by the above-described process containing L-685,487, said broth exhibiting a positive inhibition of T-cell activation by the T-cell proliferation assay.

In addition, there is provided the immunosuppressant product produced by the above-described process.

Also provided is a pharmaceutical composition containing a therapeutically effective amount of L-685,487 in combination with a pharmaceutically acceptable, substantially non-toxic carrier or excipient.

In addition, there is provided a method of use for treating human host to prevent transplantation rejection, or for treating autoimmune disease or infectious disease comprising administering to said host a therapeutically effective amount of L-685,487.

DETAILED DESCRIPTION OF THE INVENTION AND PREFERRED EMBODIMENTS

The present invention involves the fermentation of unidentified Actinomycete MA 6474, ATCC No. 53828 together with L-683,590 to produce L-685,487. The microorganism is currently on restricted deposit under the Budapest Treaty with the American Type Culture Collection, 12301 Parklawn Drive in Rockville, Md. as ATCC No. 53828, and in the Merck Culture Collection in Rahway, N.J. as MA 6474. The physical characteristics and taxonomy, including morphological, cultural, biological and physiological characteristics are briefly described hereinbelow.

On the basis of the taxonomic analysis performed thus far, the culture has tentatively been assigned as unidentified Actinomycete. Further taxonomic characteristics are being examined to place this organism conclusively within a genus and species.

This culture grows well on routine media including (28° and 37° C.), yeast malt extract agar glycerol asparagine agar, inorganic salt starch agar, oatmeal agar, Czapek Dox, Czapek solution agar and peptone agar, and Bennett's agar, all at 28° C.

Morphology—This culture grows as a branched filamentous mycelium with a diameter of about −0.76 microns. Colonies are apaque, raised, and erose. Colony texture is rubbery on yeast malt extract agar but tends to be butyrous on other media where significant fragmentation of the mycelium is observed. The colony surface tends to be matte in appearance. No diffusible pigments were observed.

Sporangia—are predominantly short chains and range in size from 4–25 microns in diameter. Sporangia are generally visible by 21 days and tend to coalesce on glycerol asparagine agar. Spores are rod shaped with blunt ends (0.76 × 1.0 microns), non-motile and occur in long, unbranched chains of up to 150 microns in length.

Cultural Characteristics of MA 6474

| Cultural Characteristics of MA 6474 | |
|---|---|
| Oatmeal Agar | |
| Vegetative Growth: | Reverse: tan. Obverse: tan, raised growth. |
| Aerial Mycelium: | Sparse, white, powdery. |
| Soluble Pigment: | None. |
| Czapek-Dox Agar (Sucrose Nitrate Agar) | |
| Vegetative Growth: | Light yellow, matte, flat. One plate demonstrates clearing around periphery of growth. |
| Aerial Mycelium: | None. |
| Soluble Pigment: | None. |
| Egg Albumin Agar | |
| Vegetative Growth: | Yellow, flat, matte. |
| Aerial Mycelium: | None. |
| Soluble Pigment: | None. |
| Glycerol Asparagine Agar | |
| Vegetative Growth: | Reverse: Creamy yellow, flat, matte. Obverse: Same. |
| Aerial Mycelium: | None. |
| Soluble Pigment: | None. |
| Inorganic Salts-Starch Agar | |
| Vegetative Growth: | Yellow, flat, matte. |
| Aerial Mycelium: | None. |
| Soluble Pigment: | None. |
| Nutrient Tyrosine Agar | |
| Vegetative Growth: | Reverse: Tan |
| Aerial Mycelium: | None. |
| Soluble Pigment: | None. |
| Decomposition of tyrosine: | Observed in areas of heavy growth. |
| Skim Milk Agar | |
| Vegetative Growth: | Yellow-tan, flay, matte. |
| Aerial Mycelium: | None. |
| Soluble Pigment: | Light brown. |
| Hydrolysis of Casein: | Excellent. |
| Yeast Extract-Malt Extract Agar | |
| Vegetative Growth: | Reverse: tan-brown. Obverse: tan-brown, raised, rugose |
| Aerial Mycelium: | Greyish-white, powdery. |
| Soluble Pigment: | None. |
| Nutrient Agar | |
| Vegetative Growth: | Yellow-tan, raised, rugose, matte. |
| Aerial Mycelium: | None. |
| Soluble Pigment: | None. |
| Nutrient Starch Agar | |
| Vegetative Growth: | Yellow-tan, raised, rugose, matte. |
| Aerial Mycelium: | None. |
| Soluble Pigment: | None. |
| Hydrolysis of Starch: | Good. |
| Tomato Paste-Oatmeal Agar | |
| Vegetative Growth: | One plate demonstrates rugose, "heaped up" mounds of mustard-yellow vegetative growth. Second plate displays confluent brown-yellow rugose growth and also isolated mustard-yellow, rugose, "heaped up" colonies. |
| Aerial Mycelium: | Sparse white aerial mycelium on second plate cited above. |
| Soluble Pigment: | None. |
| Gelatin Stabs | |
| Vegetative Growth: | None. |
| Aerial Mycelium: | None. |
| Soluble Pigment: | None. |
| Liquefaction of gelatin: | None. |
| Peptone-Iron-Yeast Extract Agar | |
| Vegetative Growth; | Orange-brown raised rugose, erose edges. |
| Aerial Mycelium: | None. |
| Soluble Pigment: | None. |
| Melanin: | Negative. |
| $H_2S$ | Negative. |
| Czapek-Dox Agar Slants | |
| Vegetative Growth: | Colorless. |
| Aerial Mycelium: | None. |
| Soluble Pigment: | None. |
| Tryptone-Yeast Extract Broth | |
| Soluble Pigment: | None. |
| Physiological and Biochemical Characteristics | |
| Oxygen requirements (stab culture in yeast extract — dextrose + salts agar) aerobic | |
| Carbon Utilization | |
| Pridham-Gottlieb Basal Medium + 1% carbon source; graded according to standards in "Methods for Characterization of Streptomyces Species", International Journal of Systematic Bacteriology, Vol. 16, No. 3, July 1966, pps. 313–340. | |
| NS (No Carbon Source) | light growth |
| alpha-D-Glucose (Positive Control) | excellent growth |
| D-Arabinose | + |
| L-Arabinose | + |
| D-Fructose | ++ |
| L-Glucose | − |
| Inositol | − |
| alpha-D-Lactose | − |
| beta-D-Lactose | − |
| D-Maltose | ++ |
| D-Mannitol | + |
| D-Mannose | ++ |
| L-Mannose | − |
| D-Raffinose | − |
| L-Rhamnose | + |
| Sucrose | − |
| D-Xylose | ++ |
| L-Xylose | − |

All readings taken after 3 weeks incubation at 28° C., unless noted otherwise. pH of all media approximately neutral (6.8–7.2).

The present invention process can be practiced with any "L-685,487-producing" strain of Actinomycete and particularly preferred is the ATCC No. 53828 strain.

In general, L-685,487 can be produced by culturing (fermenting) the above-described "L-685,487-producing strain" in the presence of L-683,590 in an aqueous nutrient medium containing sources of assimilable carbon and nitrogen, preferably under submerged aerobic conditions (e.g. shaking culture, submerged culture, etc.). The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

The L-683,590 starting material can be obtained by the fermentation of *S. hyoroscopicus var. ascomyceticus*, ATCC No. 14891, as described in U.S. Pat. No. 3,244,592, and by the fermentation of *S. hygroscopicus subsp. yakushimaensis* No. 7278, (to produce FR-900520, or "FK-520", which is identical to L-683,590) as described in EPO Publication No. 0184162 to Fujisawa, said above references hereby incorporated by reference for this particular purpose.

As to the conditions for the production of L-685,487 in massive amounts, submerged aerobic cultural conditions are preferred therefor. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of L-685,487. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of L-685,487 and is generally autoclaved to sterilize the medium prior to inoculation. The pH of the medium is generally adjusted to below pH 8.0, e.g. about 7.0, prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°–35° C., for a period of about 10 hours to 20 hours, which may be varied according to fermentation conditions and scales. Preferably, the production cultures are incubated for about 24 hours at 27° C. on a rotary shaker operating at 220 rpm., wherein the pH of the fermentation medium is maintained at 7.0 to harvest.

Preferred culturing/production media for carrying out the fermentation include the following media:

|  | g/l |
|---|---|
| Seed Medium A | |
| Dextrose | 1.0 |
| Dextrin | 10.0 |
| Beef Extract | 3.0 |
| Ardamine pH | 5.0 |
| NZ Amine Type E | 5.0 |
| $MgSO_4 \cdot 7H_2O$ | 0.05 |
| $K_2HPO_4$ | 0.37 |
| Adjust pH to 7.1 | |
| Add $CaCO_3$ 0.5 g/l | |
| Transformation Medium B | |
| Glucose | 10 |
| Yeast Extract | 1 |
| Beef Extract | 1 |
| MOPS | 11.6 |
| Adjust PH to 7.2 | |

The produced L-685,487 can be recovered from the culture medium by conventional means which are commonly used for the recovery of other known biologically active substances. The L-685,487 substance produced is found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

The product L-685,487 from the fermentation exhibits positive immunosuppressive activity by the "T-cell proliferation assay" and possesses utility on this basis and exhibits the following physical characteristics:

1. White amorphous powder
2. Solubility in methanol
3. Molecular weight of 777, as determined by FAB mass spectroscopy and is consistent with the assigned molecular structure in FIG. 1.

The L-685,487 obtained according to the fermentation processes as explained above can be isolated and purified in a conventional manner, for example, extraction, precipitation, fractional crystallization, recrystallization, chromatography, and the like.

Suitable formulations of the material may also include conventional pharmaceutically acceptable biolabile esters of L-685,487, formed via the hydroxy groups on the molecule, such as the acetate.

It is to be noted that in the aforementioned fermentation reactions and the post-treatment of the fermantation mixture therein, the tautomeric isomer(s) of L-685,487 due to rearrangement of the hemiketal ring system of the L-685,487 are also included within the scope of the present invention.

The L-685,487 of the present invention possesses pharmacological activity such as immunosuppressive activity, antimicrobial activity, and the like, and therefore are useful for the treatment and prevention of the transplantation rejection of organs or tissues such as heart, kidney, liver, medulla ossium, skin, etc., graft-versus-host diseases by medulla ossium transplantation, autoimmune diseases such as rheumatoid arthritis, systemic lupus erythematosus, Hashimoto's thyroiditis, multiple sclerosis, myasthenia gravis, type I diabetes, uveitis, and the like.

The pharmaceutical composition of this invention can be used in the form of a pharmaceutical preparation, for example, in solid, semisolid or liquid form, which contains the L-685,487, of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For applying this composition to a human, it is preferable to apply if by parenteral or enteral administration. While the dosage of therapeutically effective amount of the L-685,487, varies from, and also depends upon the age and condition of each individual patient to be treated, a daily dose (calculated on the basis of a 70 kg man) of about 0.01–1000 mg, preferably 0.1–500 mg and more preferably 0.5–100 mg, of the active ingredient is generally given for treating diseases, and an average single dose of about 0.5 mg, 1 mg, 5 mg, 10 mg, 50 mg, 100 mg, 250 mg and 500 mg is generally administered.

The following examples are given for the purpose of illustrating the present invention and should not be construed as being limitations on the scope or spirit of the instant invention.

EXAMPLE 1

Microorganism and Culture Conditions

The lyophilized culture (MA 6474) ATCC No. 53828 was used to inoculate a 250 ml baffled shake flask containing 50 ml of an autoclaved (sterilized) seed medium A consisting of (in units of grams/liter) dextrin 10.0%, dextrose 1.0%, beef extract 3.0, ardamine pH (Yeast Products, Inc.) 5.0%, N-Z Amine type E 5.0%, $MgSO_4.7H_2O$ 0.05%, $KH_2PO_4$ 0.37%, and $CaCO_3$ 0.5%. The pH of the seed medium was adjusted to 7.1 before autoclaving. The seed was incubated in the seed medium at 27° C. for 72 hours on a rotary shaker operating at 220 rpm. Alternatively, when frozen vegetative mycelia or a slant source is used, the culture is incubated in the seed medium at 27° C. for 72 hours at 220 rpm. A 5.0 ml aliquot of the resulting seed medium was used to inoculate a 250 ml non-baffled shake flask containing 50 ml of the following previously autoclaved (sterilized) transformation medium B. L-683,590 was added as a solution in dimethylsulfoxide to achieve a final concentration of 0.1 mg/ml concentration. The shake flask contents were subsequently incubated for 72 hours at 27° C. on a rotary shaker operating at 220 rpm.

1. Transformation medium B consisted of (in grams/liter) glucose 10.0; yeast extract 1.0; beef extract 1.0; MOPS 11.6; where the pH was adjusted to 7.2 before autoclaving.

Isolation and Purification Procedure for the Broth

The whole broth (100 ml) of transformation media B was extracted three times with methylene chloride (3×200 ml). Methylene chloride extracts were combined, dried over sodium sulfate, and concentrated under vacuum to an oily residue. The residue was dissolved in acetonitrile and subjected to high performance liquid chromatography (HPLC) purification.

HPLC was carried out on Whatman Partisil 10 ODS-3, 9.4 mm×25 cm column and monitored at 205 nm and 225 nm at 60° C. The column was developed at 3 ml./min with linear gradient from 0.1% aqueous $H_3PO_4-CH_3CN$, 55:45 to 0.1% aqueous $H_3PO_4-CH_3CN$, 20:80 in 40 minutes. The compound was collected during repeated injections of the above described extract. The fractions at retention time 13.9 minutes were pooled, adjusted to pH 6.5 and evaporated to remove acetonitrile. The compound was further purified using a $C_{18}$ Sep-Pak (Waters Associates) and acetonitrile-water elution solvent to yield 2.4 mg. of product, designated as L-685,487.

Characterization

L-685,487 was characterized via NMR spectrometry yielding the proton NMR spectrum of FIG. 1, which also contains the assigned molecular structure.

EXAMPLE 2

T-Cell Proliferation Assay

1. Sample Preparation

Purified L-685,487, as prepared by HPLC above, was dissolved in absolute ethanol at 1 mg/ml.

2. Assay

Spleens from C57B1/6 mice were taken under sterile conditions and gently dissociated in ice-cold RPMI 1640 culture medium (GIBCO, Grand Island, N.Y.) supplemented with 10% heat-inactivated fetal calf serum (GIBCO). Cells were pelleted by centrifugation at 1500 rpm for 8 minutes. Contaminating red cells were removed by treating the pellet with ammonium chloride lysing buffer (GIBCO) for 2 minutes at 4° C. Cold medium was added and cells were again centrifuged at 1500 rpm. for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 250° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5\times10^5$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The control, being the medium without test drug, and various below-indicated dilutions of the sample (above-described purified L-683,756) to be tested were then added in triplicate wells at 20 μl/well. L-679,934 was used as a standard. The culture plates were then incubated at 37° C. in a humidified atmosphere of 5% $CO_2$—95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as percent inhibition of tritiated thymidine uptake (proliferation) as follows:

$$\% \text{ Inhibition} = 100 - \left[ \frac{\text{Mean cpm sample tested}}{\text{Mean cpm control medium}} \right] \times 100$$

The results of % inhibition at various concentrations of L-685,487 are presented in the following Table:

TABLE

| Inhibition of T-Cell Proliferation by L-685,487 | |
|---|---|
| L-685,487 (ng/ml) | % Inhibition |
| 50.0 | 99 |
| 33.0 | 99 |
| 22.0 | 98 |
| 15.0 | 92 |
| 9.9 | 88 |
| 6.6 | 71 |
| 4.4 | 39 |
| 2.9 | 10 |

TABLE-continued

| Inhibition of T-Cell Proliferation by L-685,487 | |
|---|---|
| L-685,487 (ng/ml) | % Inhibition |
| 1.9 | 10 |
| 1.3 | 9 |
| 0.87 | 0 |
| 0.58 | 0 |

Notes:
1. Mouse T cell cultures were pulsed with $^3$H-thymidine for 4 hours prior to harvesting at 48 hours.
2. Standard L-679,934 (10 ng/ml) gave 99% inhibition.
3. $IC_{50}$ = 4.9 ng/ml = 6.3 nM, for (L-685,487), and generally in the range of 6.0 to $12.0 \times 10^{-9}$ molar.
4. Inhibition of proliferation was reversed by the addition of 50 units/ml of recombinant human IL-2.

What is claimed is:

1. An immunosuppressant, designated as L-685,487, which exhibits: positive inhibition of T-cell activation by the T-cell proliferation assay, a proton nuclear magnetic spectrum as depicted in FIG. 1, and a molecular weight of 777 as determined by FAB mass spectroscopy.

Figure 2:
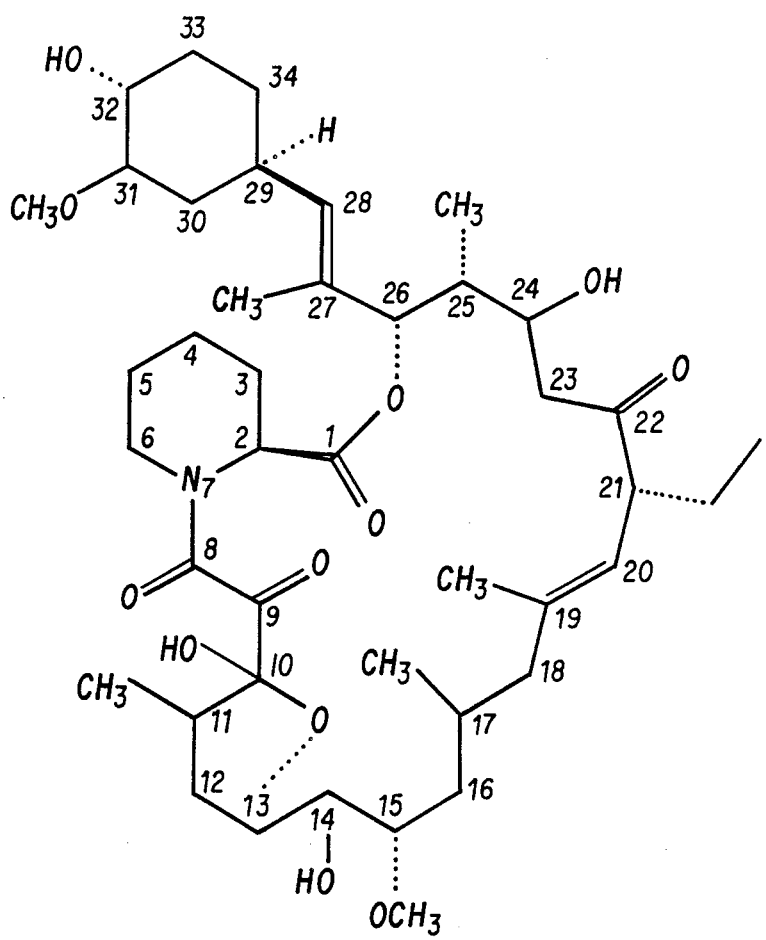
FIG. 2 is the assigned chemical structure for L-685,487.

2. An immunosuppressant, L-685,487, which has a molecular structure as depicted in FIG. 2.

3. A pharmaceutical composition useful as an immunosuppressant containing a therapeutically effective amount of L-685,487 in combination with a pharmaceutically acceptable, substantially non-toxic carrier or excipient.

4. A process for producing an immunosuppressant, identified as L-685,487, comprising the step of culturing a strain of Actinomycete, ATCC No. 53828 in the presence of L-683,590 under submerged aerobic fermentation conditions in an aqueous carbohydrate medium containing a nitrogen nutrient at a pH below 8.0 for a sufficient time to produce L-685,487.

5. The broth produced by the process of claim 4, containing L-685,487, said broth exhibiting a positive inhibition of T-cell activation by the T-cell proliferation assay.

6. The immunosuppressant product produced by the above-described process of claim 4.

7. A method of use for treating a human host to prevent transplantation rejection, or for treating autoimmune disease or infectious disease comprising administering to said host a therapeutically effective amount of L-685,487.

* * * * *